US009732324B2

(12) United States Patent
Moscona et al.

(10) Patent No.: US 9,732,324 B2
(45) Date of Patent: Aug. 15, 2017

(54) ANTI-VIRAL METHOD (75) Inventors: Anne Moscona, New York, NY (US); Matteo Porotto, New York, NY (US); David Alexander LaVan, Rockville, MD (US); Feng Yi, Rockville, MD (US)

(73) Assignee: Cornell University, Ithaca, NY (US)

( * ) Notice: Subject to any disclaimer, the term of this patent is extended or adjusted under 35 U.S.C. 154(b) by 8 days.

(21) Appl. No.: 13/125,756

(22) PCT Filed: Oct. 23, 2009

(86) PCT No.: PCT/US2009/061940
§ 371 (c)(1),
(2), (4) Date: Sep. 29, 2011

(87) PCT Pub. No.: WO2010/048572
PCT Pub. Date: Apr. 29, 2010

(65) Prior Publication Data
US 2012/0039978 A1 Feb. 16, 2012

Related U.S. Application Data (60) Provisional application No. 61/107,817, filed on Oct. 23, 2008.

(51) Int. Cl.
C12Q 1/70 (2006.01)
A61K 39/155 (2006.01)
C12N 7/00 (2006.01)

(52) U.S. Cl.
CPC ...... *C12N 7/00* (2013.01); *C12N 2760/18261* (2013.01)

(58) Field of Classification Search
None
See application file for complete search history.

(56) References Cited

U.S. PATENT DOCUMENTS

| | | | |
|---|---|---|---|
| 3,867,519 A | | 2/1975 | Michaels |
| 3,870,791 A | | 3/1975 | Haddad et al. |
| 4,051,842 A | | 10/1977 | Hazel et al. |
| 4,136,177 A | | 1/1979 | Lin et al. |
| 4,140,122 A | | 2/1979 | Kuhl et al. |
| 4,255,415 A | | 3/1981 | Chrai et al. |
| 4,383,529 A | | 5/1983 | Webster |
| 4,668,506 A | | 5/1987 | Bawa |
| 4,713,244 A | | 12/1987 | Bawa et al. |
| 4,788,063 A | | 11/1988 | Fisher et al. |
| 4,931,279 A | | 6/1990 | Bawa et al. |
| 5,484,396 A | | 1/1996 | Naficy |
| 5,753,261 A | * | 5/1998 | Fernandez et al. ........... 424/450 |
| 5,766,624 A | | 6/1998 | Janoff et al. |
| 5,785,977 A | | 7/1998 | Breithbarth |
| 5,824,268 A | * | 10/1998 | Bernstein et al. ........... 422/408 |
| 5,971,948 A | | 10/1999 | Pages et al. |
| 6,194,388 B1 | | 2/2001 | Krieg et al. |
| 6,248,514 B1 | | 6/2001 | Hutchins et al. |
| 6,268,222 B1 | | 7/2001 | Chandler et al. |
| 6,287,860 B1 | | 9/2001 | Monia et al. |
| RE37,584 E | | 3/2002 | Cham |
| 6,548,241 B1 | | 4/2003 | McBurney et al. |
| 7,011,790 B2 | | 3/2006 | Ruan et al. |
| 7,247,439 B1 | | 7/2007 | Richman et al. |
| 7,381,521 B2 | | 6/2008 | Whitaker et al. |
| 7,470,245 B2 | | 12/2008 | Tu et al. |
| 7,514,267 B1 | | 4/2009 | Lopez et al. |
| 7,527,928 B2 | | 5/2009 | Neri et al. |
| 7,592,734 B2 | | 9/2009 | Enomoto et al. |
| 2004/0005352 A1 | * | 1/2004 | Lopez et al. .................. 424/450 |
| 2004/0247624 A1 | | 12/2004 | Unger et al. |
| 2006/0154069 A1 | | 7/2006 | Lin et al. |
| 2007/0218061 A1 | | 9/2007 | Gill et al. |

FOREIGN PATENT DOCUMENTS

WO 2010048572 A1 4/2010

OTHER PUBLICATIONS

Gulick et al., Clin. Microbiol. Infect. 2003, 9:186-193.*
Brien et al., "A study of calcium carbimide-ethanol interaction in man" Europ. J. Clin. Pharmacol., 14(2):133-141 (1978).
Butler, "Fatal fruit bat virus sparks epidemics in southern Asia." Nature, 429(7):5 (2004).
Chua et al., "Nipah virus: a recently emergent deadly paramyxovirus." Science, 288: 1432-1435 (2000).
Enserink, "Emerging infectious diseases. Nipah virus (or a cousin) strikes again." Science, 303:1121 (2004).
Morris et al., "Characterization of productive and non-productive AcMNPV infection in selected insect cell lines." Virology, 197(1):339-348 (1993).
Negrete, et al. "EphrinB2 is the entry receptor for Nipah virus, an emergent deadly paramyxovirus." Nature, 436:401-405 (2005).
O'Sullivan et al., "Fatal encephalitis due to novel paramyxovirus transmitted from horses." Lancet, 349:93-95 (1997).
Wild, "Henipaviruses: a new family of emerging Paramyxoviruses." Pathol Biol (Paris). 57(2):188-96 (2009).
Porotto et al. Triggering of human parainfluenza virus 3 fusion protein(F) by the hemagglutinin-neuraminidase (HN): an HN mutation diminishing the rate of activation and fusion. J. Virol. 77, 3647-3654 (2003).

(Continued)

*Primary Examiner* — Stacy B Chen
(74) *Attorney, Agent, or Firm* — Leason Ellis LLP (57) ABSTRACT

The invention provides a method of reducing viral infectivity in a sample comprising contacting the sample with a earner matrix wherein lipids are attached to the carrier matrix, and wherein at least one virus-specific agent is attached to the lipids The virus-specific agent is capable of binding to at least one viral component The virus specific agent may be a receptor The earner matrix may be a silica particle, which may be coated with a lipid bilayer The invention further provides a method of inactivating a virus comprising contacting the virus with a earner matrix wherein lipids are attached to the earner matrix, and wherein at least one receptor is attached to the lipids, binding the receptor to at least one viral receptor-binding protein, and activating at least one viral fusion protein, wherein activation inactivates the virus, and releases the virus from the earner matrix.

14 Claims, 3 Drawing Sheets

(56) References Cited

OTHER PUBLICATIONS

Porotto, M., et al. "Inhibition of parainfluenza type 3 and Newcastle disease virus hemagglutinin-neuraminidase receptor binding: Effect of receptor avidity and steric hindrance at the inhibitor binding sites." Journal of Virology, 78:13911-13919 (2004).
Porotto et al. "Influence of the human parainfluenza virus 3 attachment protein's neuraminidase activity on its capacity to activate the fusion protein." Journal of Virology, 79:2383-2392 (2005).
Porotto, et al. "Inhibition of Hendra virus membrane fusion." Journal of Virology, 80:9837-9849 (2006).
Porotto, et al. "Molecular determinants of antiviral potency of paramyxovirus entry inhibitors." Journal of Virology, 81:10567-10574 (2007).
Russell et al. "Membrane fusion machines of paramyxoviruses: capture of intermediates of fusion." EMBO, 20:4024-4034 (2001).
Saalmüller and Mettenleiter, "Rapid identification and quantitation of cells infected by recombinant herpesvirus (pseudorabies virus) using a fluorescent-based beta-galactosidase assay and flow cytometry." J. Virol. Methods, 44:99-108 (1993).
Saxena et al., "Advances in antiviral drug discovery and development: Part II: Advancements in antiviral drug development." Future Virology, 4(3):209-215 (2009).
Sejvar et al. "Long-term neurological and functional outcome in Nipah virus infection." Annals of Neurology, 62:235-242 (2007).
Takada, et al. "A system for functional analysis of Ebola virus glycoprotein." Proceedings of the National Academy of Sciences of the United States of America, 94:14764-14769 (1997).
Virus. [online], [retrieved on Oct. 12, 2009]. Retrieved from the Internet <URL: http://en.wikipedia.org/wiki/Virus>.
Wang et al., "Molecular biology of Hendra and Nipah viruses." Microbes and infection/Institut Pasteur 3:279-287 (2001).
International Search Report for international application No. PCT/US09/61940 issued by the International Searching Authority mailed on Jan. 12, 2010.
Written Opinion of the International Searching Authority for international application No. PCT/US09/61940 issued by the International Searching Authority mailed on Jan. 12, 2010.

\* cited by examiner

FIGURE 1

FIGURE 2

ANTI-VIRAL METHOD

CROSS REFERENCE TO RELATED APPLICATION

This application claims the benefit under 35 U.S.C. §119 (e) of U.S. Provisional Application No. 61/107,817, filed on Oct. 23, 2008.

INCORPORATION-BY-REFERENCE OF SEQUENCE LISTING

A sequence listing, created on Apr. 4, 2014 as the ASCII text file "3026-087-_SeqListing_v1.txt" having a file size of 1 kilobytes, is incorporated herein by reference in its entirety.

FIELD OF THE INVENTION

The present invention relates methods of reducing viral infectivity in a sample. The present invention also relates to methods of inactivating viruses and treating viral infection.

BACKGROUND OF THE INVENTION

Paramyxoviruses have been implicated in both animal and human infections. Paramyxoviruses include mumps virus, measles virus, respiratory syncytial virus (RSV) and parainfluenza virus. RSV is the major cause of bronchiolitis and pneumonia in infants and children. Parainfluenza viruses are the second most common causes of respiratory tract disease in infants and children, and can cause pneumonia, bronchitis and croup in children and the elderly.

In 1994, a fatal infection in horses and humans in Australia was identified to be caused by a new paramyxovirus, Hendra virus (HeV). In 1998, a closely related virus, Nipah virus (NiV), was responsible for fatal infections in pigs and humans in Malaysia. Wild T. F. Henipaviruses: a new family of emerging Paramyxoviruses. *Pathol Biol (Paris)*. 57(2): 188-96 (2009). HeV and NiV, which are in the *Henipavirus* genus of the Paramyxoviridae family, are contagious and highly virulent. They are capable of infecting a number of mammalian species and causing potentially fatal disease. For example, NiV and HeV cause encephalitis in humans, with fatality rates of up to 75%. O'Sullivan et al. Fatal encephalitis due to novel paramyxovirus transmitted from horses. *Lancet* 349, 93-95 (1997). Chua et al. Nipah virus: a recently emergent deadly paramyxovirus. *Science* 288, 1432-1435 (2000). Wang et al. Molecular biology of Hendra and Nipah viruses. *Microbes and infection/Institut Pasteur* 3, 279-287 (2001). As the viruses evolve, they can now be directly transmitted from its fruit bat mammalian reservoir to humans, bypassing the pig host which served as an intermediate. Human-to-human transmission has also become a primary mode of NiV spread. Enserink, M. Emerging infectious diseases. Nipah virus (or a cousin) strikes again. *Science* 303, 1121 (2004). Butler, D. Fatal fruit bat virus sparks epidemics in southern Asia. *Nature* 429, 7 (2004). In addition to acute infection, both NiV and HeV can cause asymptomatic infection in up to 60% of exposed population, which may lead to late-onset disease or relapse of encephalitis years after initial infection, as well as persistent or delayed neurological sequelae. Sejvar et al. Long-term neurological and functional outcome in Nipah virus infection. *Annals of Neurology* 62, 235-242 (2007).

Paramyxoviruses have viral envelopes covering their protein capsids. The nucleocapsid core is composed of the genomic RNA, nucleocapsid proteins, phosphoproteins and polymerase proteins. The viral envelopes typically are derived from portions of the host cellular membranes (phospholipids and proteins), further containing some viral glycoproteins. Glycoproteins on the surface of the viral envelope can bind to receptors on the host cellular membrane. To initiate infection, the lipid bilayer of an enveloped virus fuses with a cellular membrane for delivery of the viral nucleocapsid to the host cell cytoplasm.

Specifically, the first step in the infection of a cell by HeV or NiV is the binding of the virus to the target cells, via interaction of the viral receptor-binding protein G (HeV G) with the specific cellular receptors, namely, receptor Ephrin B2 (EFNB2) for HeV, EFNB2 and EFNB3 for NiV. Then the viral fusion protein F (HeV F) mediates the fusion of the viral envelope with the plasma membrane of the cell. Upon binding to the cellular receptor, HeV G triggers HeV F to convert from its native state to fusion-activated form with the fusion domain exposed. The correct timing of HeV F activation is critical for viral entry: activation must occur only when HeV F is in contact with the target cell membrane. Porotto et al. Influence of the human parainfluenza virus 3 attachment protein's neuraminidase activity on its capacity to activate the fusion protein. *Journal of virology* 79, 2383-2392 (2005). Porotto et al. Triggering of human parainfluenza virus 3 fusion protein (F) by the hemagglutinin-neuraminidase (FIN): an I-IN mutation diminishing the rate of F activation and fusion. *J. Virol.* 77, 3647-3654 (2003). Russell et al. Membrane fusion machines of paramyxoviruses: capture of intermediates of fusion. *EMBO* 20, 4024-4034 (2001).

Although HeV and NiV were discovered in the 1990's, there still has been a lack of licensed vaccines or antiviral therapies against HeV or NiV. Accordingly, HeV and NiV are designated as biosafety level (BSL) 4 agents. Development of a therapy against henipavirues is in urgent need.

We have developed an approach to reduce the viral infectivity of henipavirus, where particles coated with a lipid bilayer and cellular receptors are used to inactivate henipaviruses specifically. This antiviral method can be used to treat, diminish or prevent viral infections caused by henipaviruses and other paramyxoviruses, as well as enveloped viruses in general.

SUMMARY OF THE INVENTION

It is an object of the present invention to provide a method of reducing viral infectivity in a sample comprising contacting the sample with a carrier matrix wherein lipids are attached to the carrier matrix, and wherein at least one virus-specific agent is attached to the lipids. The virus-specific agent is capable of binding to at least one viral component. The virus-specific agent can be a receptor, such as EphrinB2 (EFNB2). The virus-specific agent may be a protein, a peptide, a nucleic acid, an antigen, an antibody, an enzyme, a hormone, a chemical compound, a biopolymer, a synthetic polymer, or combinations thereof. The virus to which the present invention is applicable may be an enveloped virus, such as a paramyxovirus including a henipavirus.

The lipids of the present invention may be phospholipids, fatty acids, sterol lipids, glycero lipids, sphingo lipids, prenol lipids, saccharolipids, polyketides, or combinations thereof. The phospho lipid may be phosphatidylcholine, such as POPC (palmitoyloleyl phosphatidylcholine). The lipids may form a lipid bilayer attached to the carrier matrix. The carrier matrix may be a particle, such as a silica, nickel, polystyrene or latex particle. The particle may have a diameter between about 1 nm and about 100 μm, between about 10 nm and about 50 μm. The carrier matrix may comprise pores from about 1 nm to about 100 nm in mean diameter. At least one therapeutic agent may be further attached to the carrier matrix. The therapeutic agent can be an antiviral agent including a neuraminidase inhibitor, a viral fusion inhibitor, a protease inhibitor, a DNA polymerase inhibitor, a signal transduction inhibitor, a reverse transcriptase inhibitor, an interferon, and a virus-specific siRNA.

The methods of the present invention reduce viral infectivity in a biological sample, a medical sample, a food sample, an environmental sample, or an industrial sample. The biological sample may be a biological fluid, including blood, a blood component, a blood product, lymph, extracellular tissue fluid, cerebrospinal fluid (CSF), bone marrow, saliva, pleural fluid, milk, sputum, urine, synovial fluid and semen. The biological sample may also be a cell culture, a component of a cell culture, or a reagent that is used in cell culture. The viral infectivity may be reduced at least about 20%, or reduced at least about 50%.

It is a further object of the present invention to provide a method of inactivating a virus comprising the steps of: contacting the virus with a carrier matrix wherein lipids are attached to the carrier matrix, and wherein at least one receptor is attached to the lipids; binding the receptor to at least one viral receptor-binding protein; and activating at least one viral fusion protein, wherein activation inactivates the virus, and releases the virus from the carrier matrix. In one embodiment, the receptor is EphrinB2 (EFNB2). The viruses that can be inactivated by the present methods include enveloped viruses, such as paramyxoviruses including henipaviruses. The lipids may be phospholipids, fatty acids, sterol lipids, glycerolipids, sphingolipids, prenol lipids, saccharolipids, polyketides or combinations thereof. The lipids may form a lipid bilayer. The carrier matrix can be a particle, such as a silica, nickel, polystyrene or latex particle. The particle may have a diameter between about 1 nm and about 100 μm, or between about 10 nm and about 50 μm. The carrier matrix may comprise pores from about 1 nm to about 100 nm in mean diameter.

The present invention also provide a method of treating viral infection in a subject comprising administering to the subject a therapeutically effective amount of a carrier matrix wherein lipids are attached to the carrier matrix, and wherein at least one virus-specific agent is attached to the lipids. The carrier matrix may be administered orally, intravenously, nasally, subcutaneously, intramuscularly or transdermally. The subject to be treated can be a mammal, including a human.

DETAILED DESCRIPTION OF THE INVENTION

The present invention provides a method of reducing viral infectivity in a sample comprising contacting the sample with a carrier matrix wherein lipids are attached to the carrier matrix, and wherein at least one virus-specific agent is attached to the lipids. The virus-specific agent is capable of binding to at least one viral component. The virus-specific agent may be a cellular receptor that is capable to bind a viral receptor-binding protein. The carrier matrix may be a silica microparticle or nanoparticle, which may be coated with a lipid bilayer.

The present invention provides a method of inactivating a virus comprising the steps of: contacting the virus with a carrier matrix wherein lipids are attached to the carrier matrix, and wherein at least one receptor is attached to the lipids; binding the receptor to at least one viral receptor-binding protein; and activating at least one viral fusion protein, wherein activation inactivates the virus, and releases the virus from the carrier matrix.

The present invention also provides a preparation comprising a carrier matrix wherein lipids are attached to the carrier matrix, and wherein at least one virus-specific agent is attached to the lipids. The preparation may be a biological preparation, a medical preparation, or a pharmaceutical composition.

The present invention further provides a method for treating viral infection in a subject comprising administering to the subject a therapeutically effective amount of a carrier matrix wherein lipids are attached to the carrier matrix, and wherein at least one virus-specific agent is attached to the lipids.

Viruses to which the present invention is applicable include enveloped viruses and non-enveloped viruses. As used herein, the term "enveloped virus" refers to a virus that has an envelope, i.e., an outer lipid bilayer structure together with associated proteins on the outer surface. Enveloped viruses include, but are not limited to, paramyxovirus, herpesvirus such as herpes simplex virus (HSV), poxvirus, flavivirus, togavirus, coronavirus, hepatitis D virus, orthomyxovirus, rhabdovirus, bunyavirus, filovirus, Epstein-Barr virus (EBV), human cytomegalovirus (CMV), influenza virus, alphavirus, T lymphotrophic virus such as human T lymphotrophic virus (HTLV), measles virus, human respiratory syncytial virus (RSV), canine distemper virus, Newcastle disease virus, human parainfluenza virus (HPV), simian Mason-Pfizer viruses and retrovirus. Retroviruses include human immunodeficiency virus (HIV), lentivirus, Moloney murine leukemia virus (MMLV), hepadnavirus such as hepatitis B viruses, human T-lymphocyte viruses (HTLV), bovine leukosis virus, feline sarcoma virus, feline leukemia virus, simian immunodeficiency virus (SIV), simian sarcoma virus, simian leukemia, and sheep progress pneumonia virus. Non-enveloped viruses include, but are not limited to, adenovirus, parvovirus, picomavirus such as poliovirus, hepatitis A virus, enteroviruses, echoviruses, coxsachie viruses, papovaviruses such as papilloma virus, and reovirus.

In one embodiment, the present invention relates to the *Henipavirus* genus of the Paramyxoviridae family.

Viruses to which the present invention is applicable include dsDNA viruses, ssDNA viruses, dsRNA viruses, (+) ssRNA viruses RNA (e.g. picornaviruses), (−) ssRNA viruses, ssRNA-RT viruses (i.e., (+) sense RNA with DNA intermediate in life-cycle, e.g. Retroviruses), dsDNA-RT viruses.

As used herein, the term "therapeutically effective amount" is intended to include an amount of the carrier matrix coated with lipids and virus-specific agent of the present invention or an amount of the combination of agents including the carrier matrix coated with lipids and virus-specific agent, that is effective to treat or prevent viral infection, or to treat the symptoms of viral infection in a host. Therapeutically effective amount of the present pharmaceutical compositions can be determined by a person of ordinary skill in the art (such as a physician) without undue experimentation. The term "treatment" or "treating" as used herein refers to alleviating the symptoms of viral infection, arresting or relieving continued development of viral infection.

As used herein, the term "carrier matrix" refers to any material which is insoluble in water or an assay solution, and which is not highly reactive with any component likely to be found in an assay solution. The carrier matrix is made of relatively stable and inert materials that provide a support for lipids and the virus-specific agent. The carrier matrix may be a particle, bead, cover slip, slide, tube, microtiter well, sheet, chip, reaction tray, strip, membrane, film, fiber, plate, bottle, box, or any other shape suitable for the present invention. When the carrier matrix is a particle, the particle can be of substantially spherical, cubic, ovoid, rhomboid, rod-like, closed cylinder, irregular shape, or any other suitable shape. The particle may be a microparticle or nanoparticle. The diameter of the particle may be from about 1 nm to about 100 µm, from about 10 nm to about 50 µm, from about 100 nm to about 30 µm, from about 500 nm to about 20 µm, or from about 700 nm to about 10 µm.

The carrier matrix can consist of natural, semi-synthetic or synthetic materials. The carrier matrix can be made of non-biodegradable materials including, but not limited to, silica, latex, glass, quartz, metal, mica, plastic, derivatized plastic, ceramic, carbon, bentonite, alumina, borosilicate, zeolites, or combinations thereof. The carrier matrix can be made of polyester, polycarbonate, polysulfone, polyvinyl chloride, polyethylene, polypropylene, poly(N-vinyl pyrrolidone), poly(methyl methacrylate), poly(vinyl alcohol), poly(acrylic acid), polyacrylamide, poly(ethylene-co-vinyl acetate), Hydron (polymethylmethacrylate available commercially as "Hydron NCC" non-adhesive cell culture media, from Hydro Med Sciences, 8 Cedar Brook Drive, Cranbury, N.J.), poly(methacrylic acid), and combinations thereof.

The carrier matrix can be made from biodegradable materials such as starch, cross-linked starch, poly(ethylene glycol), polyvinylpyrrolidine, polylactides (PLA), polyglycolides (PGA), poly(lactide-co-glycolides) (PLGA), polyanhydrides, polyorthoesters, poly(DTH iminocarbonate), poly(bisphenol A iminocarbonate), polycyanoacrylate, polyphosphazene, mixtures thereof and combinations thereof. European Patent Application Nos. 0184899 and 0186947.

The carrier matrix may contain polystyrene, polysuflone, polyurethane, and polytetrafluoroethylene (PTFE), polyacrylate and their derivatives, copolymers (e.g. Eupergit and Dynospheres), protein (such as gelatin), polysaccharides (such as dextran, agarose, cellulose, nitrocellulose), acrylic, or mixtures thereof.

In one embodiment, the carrier matrix is a silica microparticle or nanoparticle. Examples of commercially available microparticles of suitable size are Degussas silica microparticles Aerosil. The carrier matrix may also be a latex particle or a nickel particle.

The carrier matrix may either be substantially non-porous, meso-porous, such as semi-porous, or porous. The particles of the present invention may have pores from about 1 nm to about 100 nm, from about 5 nm to about 80 nm, from about 10 nm to about 60 nm, or from 15 nm to about 50 nm in mean diameter. Materials with gel structure in the hydrated state may be used as well.

Carrier matrix of the invention may also comprise additive compound that may provide additional properties to the participle. Such additives include magnetite that impart paramagnetic characteristics, or fluorescent dyes. The carrier matrix may contain magnetic or nonmagnetic metal.

The surface of the carrier matrix may be modified with functional groups, such as alkyl, aromatic, hydroxyl, epoxy, aldehyde, amino, carboxylate and ester groups.

Lipids for use in the present invention include lipids that can spontaneously form a bilayer in an aqueous solution, and lipids that are not able to form a bilayer. Bilayer-forming lipid in general contains a hydrophobic moiety that can be in contact with the interior, hydrophobic region of the bilayer membrane, and a hydrophilic head moiety oriented toward the exterior, polar surface of the bilayer membrane. There are a variety of synthetic and naturally-occurring lipids, which may be saturated or partially unsaturated.

The lipids of the present invention may be neutral lipids, anionic lipids, or cationic lipids. The lipids of the present invention may be phospho lipids, fatty acids, sterol lipids, glycerolipids, sphingo lipids, prenol lipids, saccharolipids, glyco lipids, polyketides and combinations thereof. In some embodiments, the lipid bilayer can be made from saturated or unsaturated fatty acids. The chain length of the fatty acids, or the fatty acyl chains in the phospholipids, may range from 3 to 28 carbons. The lipids can have two hydrocarbon chains, typically acyl chains, and a head group, either polar or nonpolar. The phospho lipids may be phosphatidylcholine (PC), phosphatidyl ethanolamine (PE), phosphatidylinositol (PI), phosphatidyl glycerol (PG), phosphatidic acid (PA), phosphatidyl serine (PS), and sphingomyelin (SM), where the two hydrocarbon chains are typically between about 14-22 carbon atoms in length, and have varying degrees of unsaturation. Sterol lipids include cholesterol, sterols and steroids. Phosphatidylcholines include POPC (palmitoyloleyl phosphatidylcholine). dipalmitoyl phosphatidylcholine (DPPC), dilauryl phosphatidylcholine (DLPC), dimyristoyl phosphatidylcholine (DMPC), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC), dipalmitoleoyl phosphatidylcholine, and linoleoyl phosphatidylcholine. Lipids of the present invention may also contain dipalmitoyl phosphatidylethanolamine, dioleoylphosphatidylethanolamine (DOPE), dioleoyl phosphatidylglycerol (DOPG), palmitoyloleoyl phosphatidylglycerol (POPG), distearoylphosphatidylserine (DSPS), soybean lecithin, egg yolk lecithin, egg phosphatidyl choline (EPC), 1,2-dimyristoyl-sn-glycero-3-phosphocholine (DMPC), dimyristoyl phosphatidylglycerol, 1,2-dimyristoyl-sn-glycero-3-[phospho-rac-(1-glycerol)] (DMPG), sphingomyelin, or diphosphatidyl glycerol.

Other lipids that can be used in the present invention include, but are not limited to 1,2-diacyl-sn-glycero-3-[phospho-rac-(1-glycerol)], 1,2-diacyl-sn-glycero-3-[phospho-L-serine], 1,2 diacyl-sn-glycero-3-phosphocholine, 1,2-diacyl-sn-glycero-3-phosphate, 1,2-diacyl-sn-glycero-3-phosphoethanolamine where the diacyl groups may be symmetrical, asymmetrical and contain either saturated or unsaturated fatty acids of various types ranging from 3 to 28 carbons in chain length.

The lipids of the present invention may contain a cationic lipid. Such cationic lipids typically have a lipophilic moiety, such as a sterol, an acyl or diacyl chain. The head group of the lipid can carry a positive charge. Exemplary cationic lipids include 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy) propyl]-N,N-dimethyl-N-hydroxy ethylammonium bromide (DORIE); N-[1-(2,3-dioleyloxy) propyl]-N,N,N-trimethylammonium chloride (DOTMA); 3 [N—(N',N'-dimethylaminoethane) carbamoly]cholesterol (DC-Chol); and dimethyldioctadecylammonium (DDAB). The cationic lipid may also be a neutral lipid (such as DOPE) or an amphipathic lipid (such as a phospho lipid) derivatized with a cationic lipid, such as polylysine or other polyamine lipids. For example, the neutral lipid DOPE can be derivatized with polylysine to form a cationic lipid. U.S. Pat. Nos. 7,514,267 and 6,287,860.

The lipids attached to the carrier matrix can contain one type of lipid, or more than one type of lipid. The lipids can be obtained commercially, or prepared according to published methods that are generally known in the art.

In some embodiments, it may be helpful to utilize a lipid bilayer that contains a lipid with a covalently attached linker. Alternatively, such a linker can be attached to the carrier matrix. Such linkers can include, for example, an alkylene chain, a peptide, a glycan, a lipid, biotin or streptavidin. In some embodiments, the linker is also attached to a virus-specific agent.

The attachment of the lipids to the carrier matrix may be accomplished by a covalent bond or non-covalent bond, such as by ionic bond, hydrogen bond, hydrophobic bond, coordination, adhesive, and physical absorption. Carrier matrix coated with a lipid bilayer(s) is readily made by forming lipid vesicles containing the selected lipids in a suitable aqueous medium, followed by adding the selected carrier matrix (e.g., microparticles) and vigorously mixing the lipid vesicles with the microparticles.

Specifically, the selected lipids may be stored or dissolved in an organic solvent to facilitate handling and accurate dispensing of desired amounts of a selected lipid. After the desired composition of lipids is generated, any organic solvent used to dissolve the lipids (or mixture of lipids) can be removed by available procedures such as by drying the lipids under a stream of inert gas (e.g., nitrogen) and/or use of a vacuum. The dry lipids can be hydrated by addition of an aqueous solution or buffer followed by the vigorous mixing (e.g., sonication) for a time sufficient enough (e.g., for about 10-60 min.) not only to hydrate the lipids in the aqueous solution but also to form lipid bilayer vesicles. In general, excessive heating is avoided, and the hydration and vesicle forming procedure is performed at a temperature that is above the transition temperature of the lipid components of the vesicle. However, the temperature at which this procedure is performed should be adjusted to accommodate the type of lipid utilized with consideration for its glass transition temperature.

After formation of lipid vesicles, lipid bilayers are formed around microparticles by vigorous mixing of the microparticles with a suspension of lipid vesicles for a time sufficient to mix the microparticles with the lipids (e.g., about 5 to about 60 minutes, or from about 15 to about 45 minutes). The microparticle suspension is then incubated without vortexing for a time sufficient to coat the microparticles with lipid bilayers (about 2 to 20 minutes, or in some embodiments about 3 to 10 minutes). Excess lipids and other materials can be removed by rinsing or washing the lipid coated microparticles in a selected aqueous medium (e.g., a suitable buffer). Such rinsing or washing can be performed by repeated suspension of the lipid bilayer coated microparticles in a selected aqueous medium, centrifugation of the lipid bilayer coated microparticles particles, and decanting the aqueous supernatant. U.S. Pat. No. 7,514,267

A virus-specific agent may be attached to the carrier matrix or the lipids. The virus-specific agent is capable of binding to a viral component. The viral component may be associated with specific type(s) of viruses, or may be specific for viruses in general but not cells. As used herein, the term "virus-specific agent" refers to a molecule or entity that can be used to bind, identify, detect, target, monitor, or modify at least one viral component. The virus-specific agent can be, for example, a receptor, an antigen, an antibody, an antibody fragment (e.g., Fab, nanobodies), an aptamer, a hapten, an enzyme, a hormone, a chemical compound, a peptide, a protein, a protein fragment, a sugar (i.e., lectins), a nucleic acid, a biopolymer, a synthetic polymer, a pathogen, a microorganism or a component thereof, a toxin, a surface modifier, and combinations thereof.

A virus may recognize a receptor at the cell surface in order to invade the cell. The virus-specific agent may be a receptor. The receptor may be capable of binding to a viral receptor-binding protein. As used herein, the term "receptor" is a molecule capable of specifically binding to a ligand (e.g., a viral component). "Receptors" include, but are not limited to, biological, synthetic or engineered membrane receptors, molecular mimics, molecular imprints, molecular recognition units, cellular receptors, and congeners, analogs, derivatives or variants of these molecules. Receptors further include molecules capable of specifically recognizing viral structural molecules, effector molecules or any derivative or variant thereof. Many cell receptors recognized by viruses are known.

Examples of receptors of the present invention include, but are not limited to, Ephrin B2 (EFNB2), cell adhesion molecules (CAMs), CD4, CCR5, MHC class I molecule, mCAT1, CXADR (Coxsackie virus and adenovirus receptor), HAVCR1 (Hepatitis A virus cellular receptor 1), ACE2 (angiotensin-converting enzyme 2), transferrin receptor 1, low density lipoprotein receptor, and the like.

In one embodiment, the carrier matrix is a silica particle coated with a lipid bilayer. Ephrin B2, the cellular receptor for HeV virus, is further attached to the lipid bilayer. Ephrin B2 is able to bind to HeV G, the viral receptor-binding protein of HeV.

The virus-specific agent may be an antibody, which is capable of binding to a viral component.

As used herein, the terms "component of a virus" or "viral component" refer to, for example, a receptor-binding protein, an antibody, a hapten, an enzyme, a biopolymer, an antigen, a nucleic acid (DNA or RNA), combinations thereof, and like components. The viral component may be positioned on the surface of the virus or inside the virus.

The virus-specific agents may also include, but are not limited to, neuraminidase inhibitors, viral fusion inhibitors, protease inhibitors, DNA polymerase inhibitors, signal transduction inhibitors, reverse transcriptase inhibitors (such as nucleoside reverse transcriptase inhibitors and non-nucleoside reverse transcriptase inhibitors), interferons, nucleoside analogs, integrase inhibitors, thymidine kinase inhibitors, viral sugar or glycoprotein synthesis inhibitors, viral structural protein synthesis inhibitors, viral attachment and adsorption inhibitors, viral entry inhibitors and their functional analogs. Saxena et al., *Future Virology*, 4 (3): 209-215 (2009).

Neuraminidase inhibitors may include oseltamivir, zanamivir and peramivir. Viral fusion inhibitors may include cyclosporine, maraviroc, enfuviritide and docosanol. Protease inhibitors may include saquinavir, indinarvir, amprenavir, nelfinavir, ritonavir, tipranavir, atazanavir, darunavir, zanamivir and oseltamivir. DNA polymerase inhibitors may include idoxuridine, vidarabine, phosphonoacetic acid, trifluridine, acyclovir, foscarnet, ganciclovir, penciclovir, cidofovir, famciclovi, valaciclovir and valganciclovir. Signal transduction inhibitors include resveratrol and ribavirin. Nucleoside reverse transcriptase inhibitors (NRTIs) may include zidovudine (ZDV, AZT), lamivudine (3TC), stavudine (d4T), zalcitabine (ddC), didanosine (2',3'-dideoxyinosine, ddI), abacavir (ABC), emirivine (FTC), tenofovir (TDF), delaviradine (DLV), fuzeon (T-20), indinavir (IDV), lopinavir (LPV), atazanavir, combivir (ZDV/3TC), kaletra (RTV/LPV), adefovir dipivoxil and trizivir (ZDV/3TC/ABC). Non-nucleoside reverse transcriptase inhibitors (NNRTIs) may include nevirapine, delavirdine, UC-781 (thiocarboxanilide), pyridinones, TIBO, calanolide A, capravirine and efavirenz. Viral entry inhibitors may include Fuzeon (T-20), NB-2, NB-64, T-649, T-1249, SCH-C, SCH-D, PRO 140, TAK 779, TAK-220, RANTES analogs, AK602, UK-427, 857, monoclonal antibodies against relevant receptors, cyanovirin-N, cyclodextrins, carregeenans, sulfated or sulfonated polymers, mandelic acid condensation polymers, AMD-3100, and functional analogs thereof.

The virus-specific agents may also include, but are not limited to, the following: cemannan; alovudine; alvircept sudotox; aranotin; arildone; atevirdine mesylate; avridine, carbovir, cipamfylline; clevadine, crixivan, cytarabine; desciclovir; dideoxyino sine, dideoxycytidine, disoxaril, edoxudine; enfuvirtide, entecavir, enviradene; enviroxime; famciclovir; famotine; fiacitabine; fialuridine; floxuridine, fosarilate; fosfonet, gancyclovir, kethoxal; levovirin, lobucavir; lopinovir, memotine, methisazone; moroxydine, pirodavir, pleconaril, podophyllotoxin, rimantadine, sequanavir, somantadine, sorivudine, stallimycine, statolon; tilorone; tromantadine, valacyclovir, viramidine, viroxime, xenazoic acid, zalcitabine; zerit, zinviroxime, pyridine, α-methyl-1-adamantanemethylamine, hydroxy-ethoxymethylguanine, adamantanamine, 5-iodo-2'-deoxyuridine, trifluorothymidine, adenine arabinoside, 2',3'-dideoxynucleosides such as 2',3'-didoxycytidine, 2',3'-dideoxyadenosine, 2',3'-didoxyinosine, 2',3'-didehydrothymidine, co-trimoxazole, 9-[2-(R)-[[bis[[(isopropoxy-carbonyl)oxy]-methoxy]phosphinoyl]methoxy]propyl]adenine, (R)-9-[2-(phosphonomethoxy)-propyl]adenine, tenofivir disoproxil, TAT inhibitors such as 7-chloro-5-(2-pyrryl)-3H-1,4-benzodiazepin-2(H)-one or nucleic acids that comprise one or more unmethylated CpG sequences essentially as disclosed in, e.g., U.S. Pat. No. 6,194,388.

The virus-specific agents may be attached to the lipids or to the carrier matrix. The attachment of the virus-specific agents to the lipids or the carrier matrix may be accomplished by a covalent bond or non-covalent bond, such as by ionic bond, hydrogen bond, hydrophobic bond, coordination, adhesive, and physical absorption. The virus-specific agents can be attached to a linker or spacer that is attached to the carrier matrix or the lipids. Such a linker can help to optimally position the virus-specific agents for interaction with the viral component. The linkers can include, for example, an alkylene chain, a peptide, a glycan, a lipid, biotin or streptavidin. The virus-specific agent may be attached to the carrier matrix by, for example, coupling reactions using carbodiimide, carboxylates, esters, alcohols, carbamides, aldehydes, amines, sulfur oxides, nitrogen oxides, halides, or any other suitable compound known in the art. U.S. Pat. No. 6,268,222.

The lipids may contain a metal ion-chelating lipid to accommodate the binding of the virus-specific agent. For example, a nickel-chelating lipid, such as the nickel salt of 1,2-dioleoyl-sn-glycero-3-{[N(5-amino-1-carboxypentyl)iminodiacetic acid] (DOGS-NTA-Ni), may be used to bind histidine-tagged receptor protein.

The fluidity of the lipid coating, the density and distribution of the virus-specific agents on the carrier matrix surface may be adjusted for different needs.

The carrier matrix may further contain a therapeutic agent. The therapeutic agent may be attached to the carrier matrix covalently or non-covalently.

As used herein, the term "therapeutic agent" refers to a substance that may be used in the diagnosis, cure, mitigation, treatment, or prevention of disease in a human or animal. Such therapeutic agents include substances recognized in the official United States Pharmacopeia, official Homeopathic Pharmacopeia of the United States, official National Formulary, or any supplement thereof.

Therapeutic agents that can be incorporated with the present preparation include nucleosides, nucleoside analogs, siRNA, oligopeptides, polypeptides, COX-2 inhibitors, apoptosis promoters, urinary tract agents, vaginal agents, vasodilators neurodegenerative agents (e.g., Parkinson's disease), obesity agents, ophthalmic agents, osteoporosis agents, para-sympatholytics, para-sympathometics, antianesthetics, prostaglandins, psychotherapeutic agents, respiratory agents, sedatives, hypnotics, skin and mucous membrane agents, anti-bacterials, anti-fungals, antineoplastics, cardioprotective agents, cardiovascular agents, anti-thrombotics, central nervous system stimulants, cholinesterase inhibitors, contraceptives, dopamine receptor agonists, erectile dysfunction agents, fertility agents, gastrointestinal agents, gout agents, hormones, immunomodulators, suitably functionalized analgesics or general or local anesthetics, anti-convulsants, anti-diabetic agents, anti-fibrotic agents, anti-infectives, motion sickness agents, muscle relaxants, immuno-suppressive agents, migraine agents, non-steroidal anti-inflammatory drugs (NSAIDs), smoking cessation agents, or sympatholytics (see Physicians' Desk Reference, 55th ed., 2001, Medical Economics Company, Inc., Montvale, N.J., pages 201-202).

The present invention provides a method of reducing viral infectivity comprising contacting the virus with a carrier matrix wherein lipids are attached to the carrier matrix, and wherein at least one virus-specific agent is attached to the lipids. The viral infectivity may be reduced at least about 10%, at least about 20%, at least about 30%, at least about 40%, at least about 50%, from about 10% to about 100%, from about 20% to about 100%, from about 30% to about 100%, from 40% to about 100%, or from about 50% to about 100%.

Viral infectivity can be measured using various methods and techniques that are known by one of ordinary skill in the art. For example, the reduction in viral infectivity can be demonstrated by reduction of the viral titer, or inhibition of virus replication. Viral titer can be quantitated by routine applications, such as ELISA, flow cytometry, quantitative PCR, RT-PCR or TaqMan assays. U.S. Pat. Nos. 6,248,514 and 7,247,439. Cann, Alan, *Virus Culture: a Practical Approach*. Oxford University Press, 1999. Viral infectivity can be measured by plaque-forming assay that scores the number of viral plaques as a function of dilution. Viral infectivity may also be measured using the tissue culture infective dose procedure (TCID$_{50}$), which estimates infectivity as a function of intracellular staining for an antigen by direct immuno fluorescence. Flow cytometry or FACS (fluorescence-activated cell sorting) assays have been used to measure the number of infected cells in cell cultures infected at relatively high multiplicities of infection. For example, Saalmuller and Mettenleiter (J. Virol. Methods 44:99-108 (1993)) disclose the identification and quantitation of cells infected by recombinant pseudorabies virus mutants by the reaction of intracellular β-galactosidase expressed during infection with recombinant viruses with a fluorogenic substrate, followed by detection of positive cells in flow cytometry. Morris et al. (Virology 197(1):339-48 (1993)) studied the process of productive and non-productive recombinant AcMNPV infection in cultured cells by immunostaining cells to detect the reporter CAT gene product.

The methods of the present invention may be used to reduce viral infectivity in a sample, including a biological sample, a medical sample, a food sample, an environmental sample, or an industrial sample. The samples that can be treated by the methods of the present invention include water and water-based solutions. The biological sample may be biological fluids including, but not limited to, blood, a blood component (e.g., blood cells, plasma proteins, serum, plasma, etc.), blood products, lymph, extracellular tissue fluid, cerebrospinal fluid (CSF), bone marrow, saliva, pleural fluid, milk, sputum, urine, synovial fluid and semen. The biological sample may be cell culture, a component of a cell culture, or any solution, liquid or reagent that are used in cell culture. The biological sample may be biological tissues such as skin and organs for transplantation. The present invention also relates to applications via the blood circulatory system for controlling the pathological state produced by viruses. A biological sample may be treated by the methods of the present invention so that it may be used safely and effectively for diagnostic, therapeutic or research purposes. Biological samples may be from a human or an animal. A "biological sample" obtained from a patient can be referred to either as a "biological sample" or a "patient sample". Assay of a "patient sample" using the methods in the present invention may be after the removal of cells or tissue from the patient. Alternatively, assay of a "patient sample" using the methods in the present invention need not require removal of cells or tissue from the patient. Biological samples may be obtained from various families of domestic animals, as well as feral or wild animals, including, but not limited to, horse, dog, cat, pig, rodent, monkey, etc. U.S. Pat. Nos. 7,381,521 and 7,011,790, 7,592,134 and 7,527,928.

It is a further object of the present invention to provide a filtration system to reduce viral infectivity in a sample. The filtration system may be in the form of a filter, a column, a membrane prepared using the present arrier matrix coated with lipids and virus-specific agent. For example, silica particles coated with lipids and virus-specific agent can be packed into a column; a virus-containing sample is then loaded onto the column. The sample collected from the column will have reduced viral infectivity.

The present invention may relate to a method of extracorporeally reducing viral infectivity of a patient's blood comprising: filtering the patient's blood through a blood filtration apparatus configured for separating a plasma constituent from the blood; passing the plasma constituent through means for reducing the viral infectivity in the plasma constituent using the methods of the present invention; and returning plasma components of the patient's blood back to the patient. Extracorporeal systems that can be used in the present invention may be any extracorporeal body fluid system. The extracorporeal method is readily known to those of skill in the art, including, for example, a kidney dialysis method, a blood oxygenation method, a blood salvage process disclosed in U.S. Pat. No. 5,971,948, a delipidation process disclosed in U.S. Pat. No. 5,484,396, a solvent extraction process disclosed in U.S. Pat. No. RE 37,584, a photoradiation process disclosed in U.S. Pat. No. 6,548,241, and the like. The system may be applicable to treatment of cell-free plasma or white blood cells containing plasma, followed by removal of treated white blood cells before reinfusion into a patient. U.S. Pat. No. 7,470,245.

The methods of the present invention may be used to reduce viral infectivity in a sample including liquid and solid food and feed products and ingredients such as dairy items, vegetables, meat and meat by-products, and waste. Environmental samples include environmental material such as surface matter, soil, water. Industrial samples including samples obtained from food and dairy processing instruments, apparatus, equipment, utensils, disposable and non-disposable items. These examples are not to be construed as limiting the sample types applicable to the present invention.

The present invention also provides a method of inactivating a virus comprising the steps of: contacting the virus with a carrier matrix wherein lipids are attached to the carrier matrix, and wherein at least one receptor is attached to the lipids; binding the receptor to at least one viral receptor-binding protein; and activating at least one viral fusion protein, wherein activation inactivates the virus, and releases the virus from the carrier matrix.

In one embodiment, HeV viruses are inactivated by contacting the viruses with carrier matrix coated with a lipid bilayer. Cellular receptor EphrinB2 is further attached to the lipids. The lipid coating of the carrier matrix is structurally similar to biological membranes, including cell membrane and viral envelope. Without being limited to any specific physiological mechanism, it is believed that the carrier matrix coated with lipids and cellular receptors acts as a decoy to inactivate viruses. The viral component, e.g., receptor-binding protein Hev G, binds to the cellular receptor, e.g., EphrinB2, on the carrier matrix, which in turn activates the viral fusion protein F. As the lipid-coated carrier matrix can not fuse with the virus, the virus is inactivated due to premature activation of the fusion protein and is released from the carrier matrix afterwards.

The inactivation of viruses or reduction of viral infectivity using the methods of the present invention may be temperature-dependent or temperature-independent. The inactivation of viruses or reduction of viral infectivity using the methods of the present invention may be saturable or insaturable.

The present invention further provides a method for treating viral infection in a subject comprising administering to the subject a therapeutically effective amount of a carrier matrix wherein lipids are attached to the carrier matrix, and wherein at least one virus-specific agent is attached to the lipids.

In one embodiment, viral infection caused by paramyxoviruses in a subject are treated by administering to the subject a pharmaceutical composition comprising silica microparticles or nanoparticles with a lipid bilayer attached to the surfaces of the microparticles or nanoparticles. Cellular receptor EphrinB2 is further attached to the lipids. The lipids may contain phosphatidylcholine.

In certain embodiments it may be desirable to use a mixture of two or more types of carrier matrixes having different properties, such as different lipids, different virus-specific agents, or different therapeutic agents in order to exploit the benefits of targeting different components of viruses or different populations of viruses either simultaneously or sequentially.

The subjects that can be treated using the preparations and methods of this invention are mammals, including a human, horse, dog, cat, pig, rodent, monkey and the like.

The pharmaceutical compositions of the invention may be administered orally in the form of a suitable pharmaceutical unit dosage form. The pharmaceutical compositions of the invention may be prepared in many forms that include tablets, hard or soft gelatin capsules, aqueous solutions, suspensions, and liposomes and other slow-release formulations, such as shaped polymeric gels. The mode of administration and dosage forms are closely related to the properties of the therapeutic agents or compositions which are desirable and efficacious for the given treatment application. Suitable dosage forms include, but are not limited to, oral, intravenous, rectal, sublingual, mucosal, nasal, ophthalmic, subcutaneous, intramuscular, transdermal, spinal, intrathecal, intra-articular, intra-arterial, sub-arachnoid, bronchial, and lymphatic administration, and other dosage forms for systemic delivery of active ingredients. The present pharmaceutical composition may be administered by any method known in the art, including, without limitation, transdermal (passive via patch, gel, cream, ointment or iontophoretic); intravenous (bolus, infusion); subcutaneous (infusion, depot); transmucosal (buccal and sublingual, e.g., orodispersible tablets, wafers, film, and effervescent formulations; conjunctival (eyedrops); rectal (suppository, enema)); or intradermal (bolus, infusion, depot). The composition may be delivered topically.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

The pharmaceutical compositions of the invention may also be formulated for parenteral administration (e.g., by injection, for example, bolus injection or continuous infusion) and may be presented in unit dosage form in ampules, pre-filled syringes, small volume infusion containers or multi-dose containers with an added preservative. The pharmaceutical compositions may take such forms as suspensions, solutions, or emulsions in oily or aqueous vehicles, and may contain formulating agents such as suspending, stabilizing and/or dispersing agents. Alternatively, the pharmaceutical compositions of the invention may be in powder form, obtained by aseptic isolation of sterile solid or by lyophilization from solution, for constitution with a suitable vehicle, e.g., sterile, pyrogen-free water, before use.

For topical administration to the epidermis, the pharmaceutical compositions may be formulated as ointments, creams or lotions, or as the active ingredient of a transdermal patch. Suitable transdermal delivery systems are disclosed, for example, in A. Fisher et al. (U.S. Pat. No. 4,788,603), or R. Bawa et al. (U.S. Pat. Nos. 4,931,279; 4,668,506; and 4,713,224). Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The pharmaceutical compositions can also be delivered via ionophoresis, e.g., as disclosed in U.S. Pat. Nos. 4,140,122; 4,383,529; or 4,051,842.

Pharmaceutical compositions suitable for topical administration in the mouth include unit dosage forms such as lozenges comprising a pharmaceutical composition of the invention in a flavored base, usually sucrose and acadia or tragacanth; pastilles comprising the pharmaceutical composition in an inert base such as gelatin and glycerin or sucrose and acacia; mucoadherent gels, and mouthwashes comprising the pharmaceutical composition in a suitable liquid carrier.

For topical administration to the eye, the pharmaceutical compositions can be administered as drops, gels (S. Chrai et al., U.S. Pat. No. 4,255,415), gums (S. L. Lin et al., U.S. Pat. No. 4,136,177) or via a prolonged-release ocular insert (A. S. Michaels, U.S. Pat. No. 3,867,519 and H. M. Haddad et al., U.S. Pat. No. 3,870,791).

When desired, the above-described pharmaceutical compositions can be adapted to give sustained release of a therapeutic compound employed, e.g., by combination with certain hydrophilic polymer matrices, e.g., comprising natural gels, synthetic polymer gels or mixtures thereof.

Pharmaceutical compositions suitable for rectal administration wherein the carrier is a solid are most preferably presented as unit dose suppositories. Suitable carriers include cocoa butter and other materials commonly used in the art, and the suppositories may be conveniently formed by admixture of the pharmaceutical composition with the softened or melted carrier(s) followed by chilling and shaping in molds.

Pharmaceutical compositions suitable for vaginal administration may be presented as pessaries, tampons, creams, gels, pastes, foams or sprays containing, in addition to the nanoparticles and the therapeutic agent, such carriers are well known in the art.

For administration by inhalation, the pharmaceutical compositions according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the pharmaceutical compositions of the invention may take the form of a dry powder composition, for example, a powder mix of the pharmaceutical composition and a suitable powder base such as lactose or starch. The powder composition may be presented in unit dosage form in, for example, capsules or cartridges or, e.g., gelatin or blister packs from which the powder may be administered with the aid of an inhalator or insufflator.

For intra-nasal administration, the pharmaceutical compositions of the invention may be administered via a liquid spray, such as via a plastic bottle atomizer. Typical of these are the Mistometer® (isoproterenol inhaler-Wintrop) and the Medihaler® (isoproterenol inhaler-Riker).

Pharmaceutical compositions of the invention may also contain other adjuvants such as flavorings, colorings, antimicrobial agents, or preservatives.

It will be further appreciated that the amount of the pharmaceutical compositions required for use in treatment will vary not only with the therapeutic agent selected but also with the route of administration, the nature of the condition being treated and the age and condition of the patient and will be ultimately at the discretion of the attendant physician or clinician. For evaluations of these factors, see J. F. Brien et al., Europ. J. Clin. Pharmacol., 14, 133 (1978); and Physicians' Desk Reference, Charles E. Baker, Jr., Pub., Medical Economics Co., Oradell, N.J. (41st ed., 1987). Generally, the dosages of the therapeutic agent when used in combination with the fluorescent nanoparticles of the present invention can be lower than when the therapeutic agent is administered alone or in conventional pharmaceutical dosage forms. The high specificity of the fluorescent nanoparticle for a target site, such as a receptor situated on a cell's surface, can provide a relatively highly localized concentration of a therapeutic agent, or alternatively, a sustained release of a therapeutic agent over an extended time period.

The following examples are presented for the purposes of illustration only and are not limiting the invention.

Example 1

Envelope glycoprotein pseudotyped viruses were used to study the inhibition of henipavirus infection. The pseudotyped virus is vesicular stomatitis virus (a BSL2 agent) bearing the henipavirus entry molecules and uses the identical entry mechanism as live henipavirus. Porotto, et al. Molecular determinants of antiviral potency of paramyxovirus entry inhibitors. *J. Virol.* 81, 10567-10574 (2007). Porotto, et al Inhibition of Hendra virus membrane fusion. *J. Virol.* 80, 9837-9849 (2006).

Development of Microparticles Coated with Lipid Bound Receptors.

Figure 1:
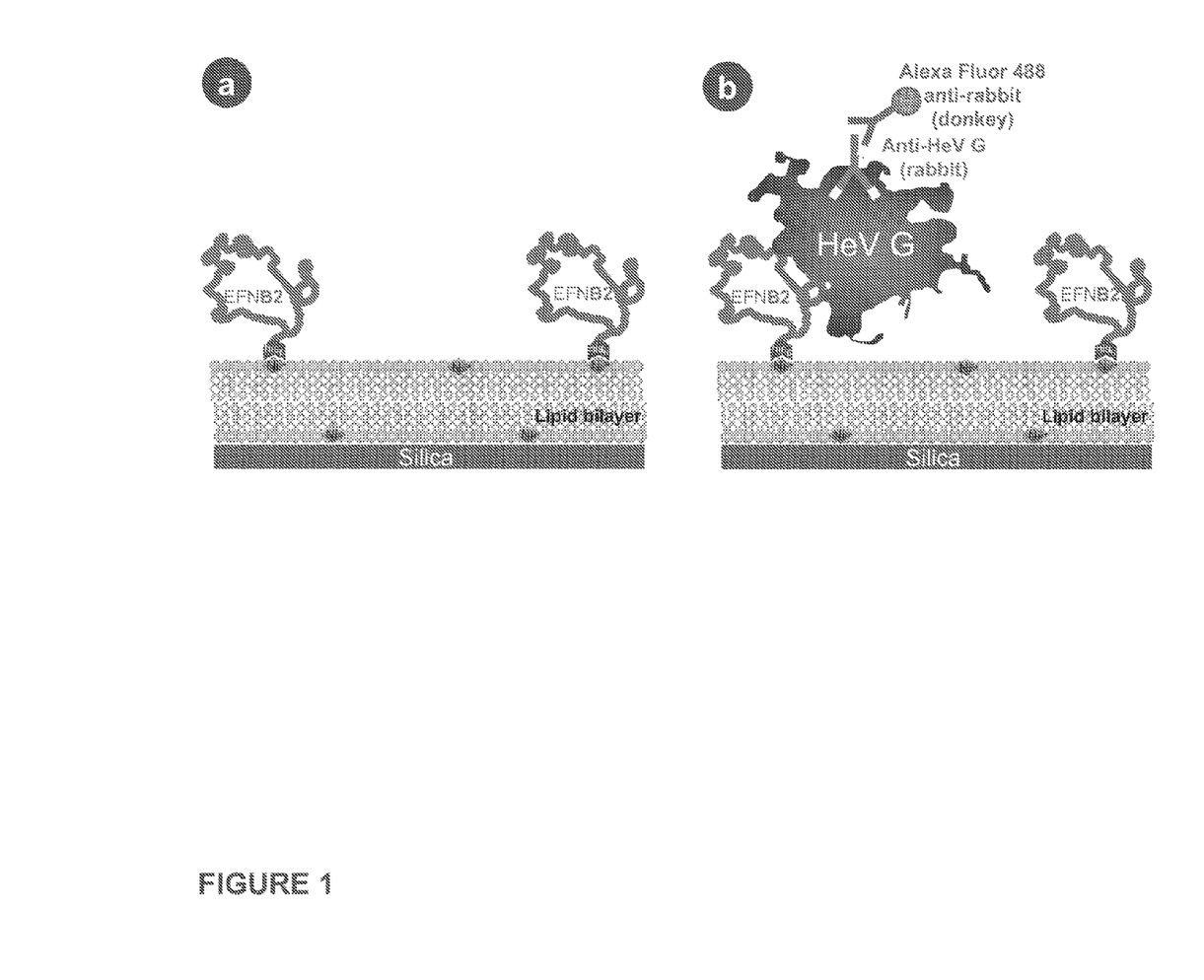
FIG. 1a shows a schematic representation of the silica microparticles coated with a lipid bilayer and EFNB2 cellular receptor.
FIG. 1b shows a scheme to detect EFNB2-coated silica microparticles using purified HeV G protein and anti-HeV G antibodies.

The strategy of construction of the microparticles bearing henipavirus entry receptors is diagrammed in FIG. 1a. Glass cover slips were coated with mesoporous $SiO_2$ layer, serving as the carrier matrix. Alternatively, mesoporous $SiO_2$ microparticles with a mean diameter of about 3 µm were used as the carrier matrix. A nickel chelating lipid (NTA lipid) bilayer was formed on the surface of the microparticle. If imaging of the lipid on the $SiO_2$ surface is desired, 1% red fluorescent-labeled POPC may be incorporated in the lipids. Polyhistidine-tagged EFNB2 was then attached to the lipids. As EFNB1 is not a receptor for HeV G receptor-binding protein, polyhistidine-tagged EFNB1 was used as a control. Purified soluble HeV G was incubated with the microparticles. The binding of Hendra G to the $SiO_2$ surface was assessed by immuno fluorescence (see the diagram in FIG. 1b) and FACS. The microparticles bearing EFNB2 efficiently bound HeV G and were fluorescent, while the microparticles bearing EFNB1 did not bind HeV G.

Receptor-Coated Microparticles Inactivated Pseudotyped Viruses and Reduced the Titer of Infective Pseudotyped HeV Virions in Cell Culture.

Figure 2:
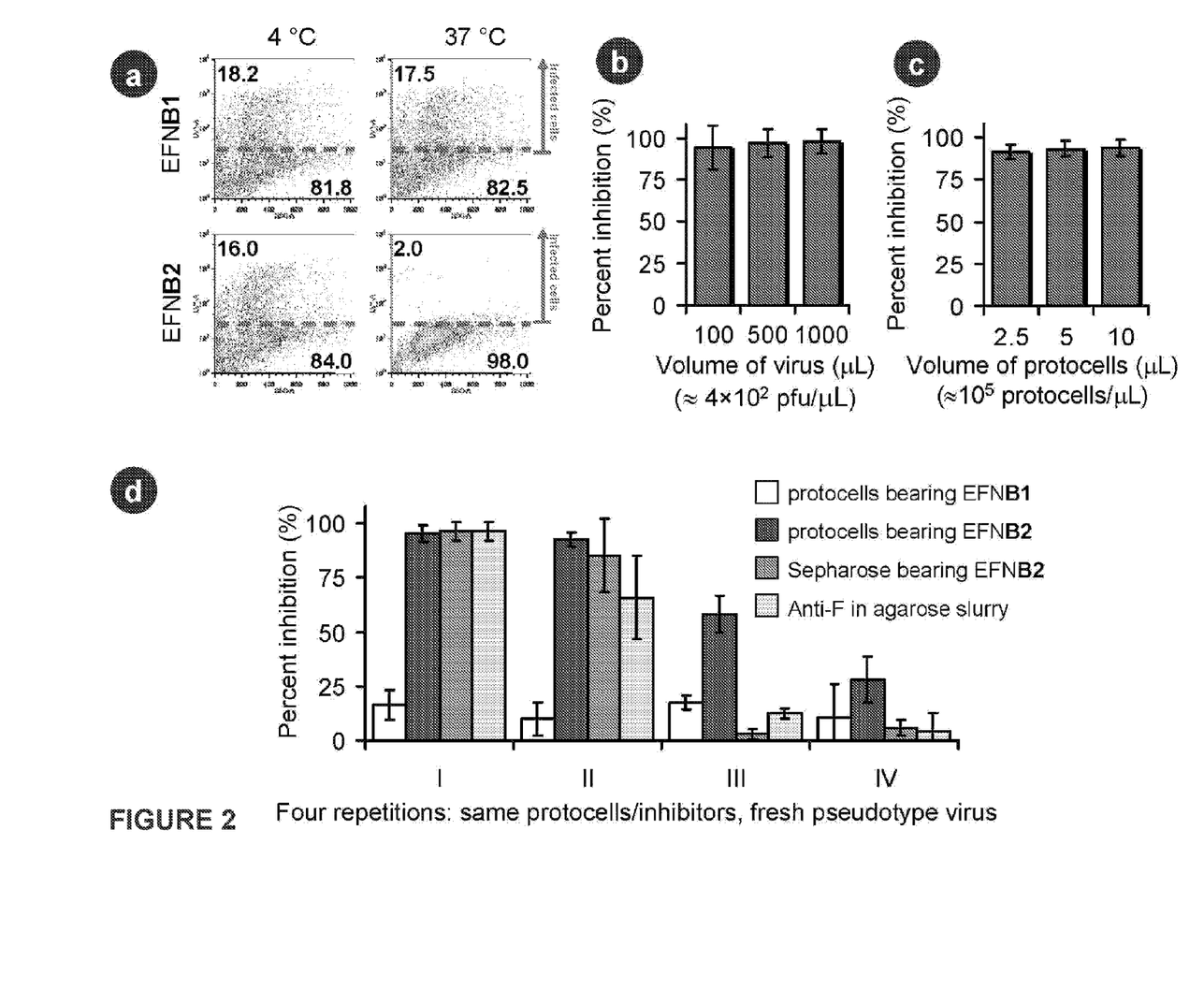
FIG. 2a shows fluorescence-activated cell sorting (FACS) results to study cells infected with pseudotyped viruses after incubation with EFNB2- or EFNB1-coated microparticles at 4° C. or 37° C. Infected cells are fluorescent and are above the dotted line, non-infected cells remain non-fluorescent and are below the dotted line.
FIG. 2b shows percent inhibition of viral titer by exposure to EFNB2-coated microparticles, after addition of varying amounts of pseudotyped virus (pfu×$10^3$). Inhibitory effect does not decrease significantly as the amount of the viruses increases.
FIG. 2c shows percent inhibition of viral titer after sequential exposure to microparticles coated with EFNB1 or EFNB2, to sepharose beads coated with EFNB2, or to sepharose beads bearing anti-F antibodies. Inhibitory effect does not decrease significantly as the amount of EFNB2-coated microparticles decreases.
FIG. 2d shows percent inhibition of viral titer after each of steps I-IV. For each step, The microparticles were washed, pelleted, and re-incubated with pseudotyped viruses. The EFNB2-bearing microparticles retain inhibitory activity after four uses. In the figures, protocells refer to silica microparticles coated with lipids and receptors.

Microparticles were incubated with pseudotyped viruses for one hour at 37° C. and then the viral titer (infectivity on cultured human cells) was assessed and compared to the titer of untreated pseudotyped viruses. Microparticles were coated with either EFNB1 or EFNB2. EFNB2-coated microparticles effectively inhibited infectivity of the HeV-pseudotyped virions, causing a dramatic decrease in viral titer after incubation with the microparticles (FIG. 2a). The inhibitory effect of the microparticles is specific for henipaviruses. Incubation with paramyxovirus human parainfluenza virus type 3, and with the rhabdovirus vesicular stomatitis virus, each of which uses a different entry receptor, did not result in a decrease in viral titer, confirming the specificity of inhibition. Pseudotyped viruses were incubated with EFNB2 or EFNB1-coated microparticles at 4° C. or 37° C., and then used to infect human cells. In parallel, pseudotyped viruses were incubated with EFNB2-bearing sepharose beads at 4° C. or 37° C., and then used to infect human cells. FACS analysis was then carried out to determine the percentage of infected cells. The cells that were infected by the pseudotyped viruses (after the various incubations) are fluorescent, which is shown in the top section of each panel in FIG. 2a. When viruses were treated at 37° C. with EFNB2-coated microparticles before exposure to cells, the percentage of infected cells greatly decreased (lower right panel of FIG. 2a). For viruses incubated with EFNB1-coated microparticles at either 4° C. or 37° C., and for viruses incubated with EFNB2-coated microparticles at 4° C., the number of infected cells was approximately the same, at 18.1%, 17.5%, and 16.0%, respectively. For viruses incubated with EFNB2-coated microparticles at 37° C., only 2.0% of cells were infected. At 4° C., neither EFNB1 nor EFNB2-bearing microparticles inhibit viral infectivity, while at 37° C., the EFNB2-coated, but not the EFNB1-coated, microparticles are inhibitory. In contrast, the EFNB2-bearing sepharose beads inhibited infection equally at 4° C. or 37° C. These results show that inhibition of viral infectivity by receptor-coated microparticles may be temperature-dependent.

The Receptor-Coated Microparticles are not Saturable, but Continue to Inactivate Pseudotyped Viruses in a "Re-Usable" Fashion.

EFNB2-bearing microparticles or, in parallel, sepharose beads bearing EFNB2, were incubated with pseudotyped viruses in concentrations ranging from 1 to 10 plaque forming units (pfu) per microparticle. After incubation, the supernatant fluid was collected and titered for infectious pseudotyped viruses. The anti-viral activity of the EFNB2-bearing microparticles was retained after several uses, regardless of the concentration of virus (FIG. 2b) or concentration of microparticles (FIG. 2c). To assess whether the microparticles retain activity after repeated use, the EFNB2- bearing microparticles and EFNB2-bearing sepharose beads, along with microparticles bearing EFNB1 and sepharose beads bearing anti-F protein antibodies, were washed, incubated with new pseudotyped viruses, and re-titered (FIG. 2d). For each repetition (I-IV) the used microparticles were washed, pelleted, and incubated with new pseudotyped viruses. For the EFNB2-bearing microparticles, activity vs. pseudotyped viruses was retained, regardless of the number of incubations. The red bars in FIG. 2D show that EFNB2-bearing microparticles retain inhibitory activity even at the fourth re-incubation. In contrast, as shown by the blue and green bars in FIG. 2d, the efficacy of the sepharose beads bearing EFNB2 or anti-F antibodies was already decreased at the second re-incubation, and was reduced upon each re-incubation, with no inhibitory effect observed after the third use.

Virus Inactivation by Receptor-Coated Microparticles Requires Interaction of EFNB2 Receptor and Viral Receptor-Binding Protein Hendra-G, but is not Attributable to Hendra-G Binding Alone.

Figure 3:
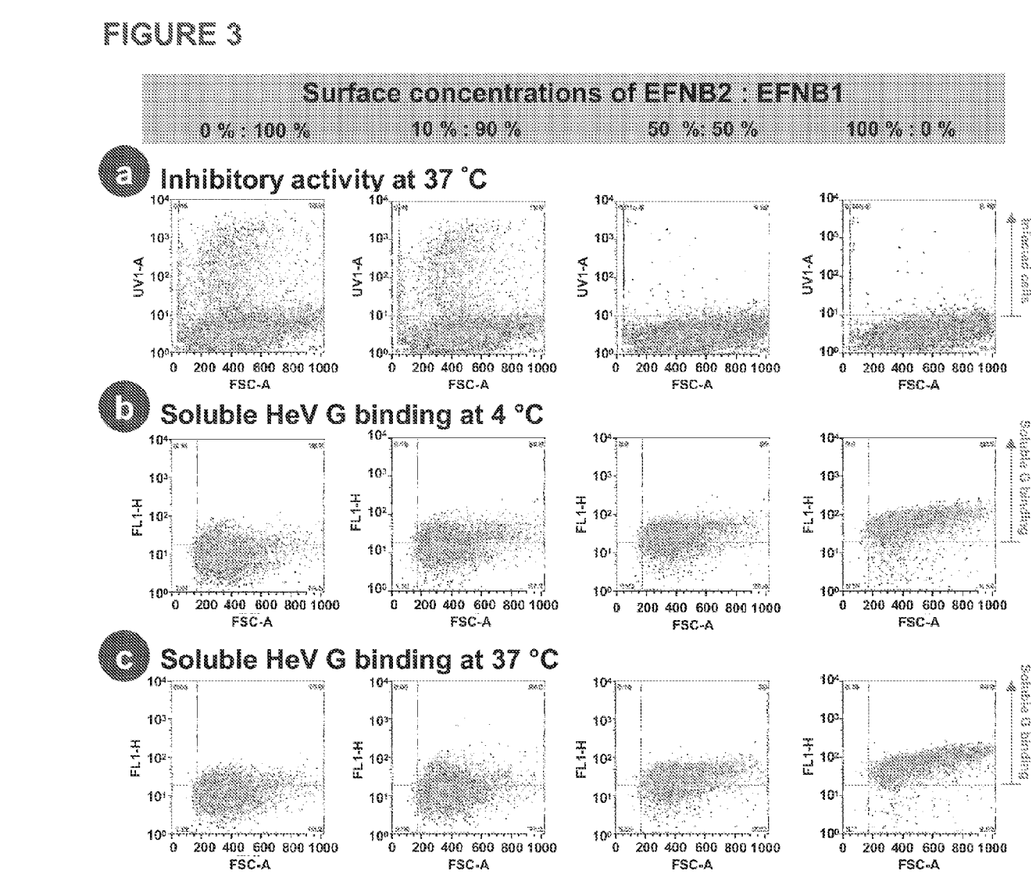
FIG. 3a shows the FACS results to study cells infected with pseudotyped viruses after incubation with microparticles coated with various ratios of EFNB1: EFNB2 at 37° C. Infected cells are fluorescent and are shown in the upper sections.
FIG. 3b shows the FACS results to study binding of soluble HeV G to microparticles coated with various ratios of EFNB1: EFNB2 at 4° C. Microparticles bound to soluble HeV G are fluorescent, and are shown in the upper sections.
FIG. 3c shows the FACS results to study binding of soluble HeV G to microparticles coated with various ratios of EFNB1: EFNB2 at 37° C. Microparticles bound to soluble HeV G are fluorescent, and are shown in the upper sections.

We further studied whether there is any correlation between the surface concentration of EFNB2 on microparticles and their antiviral effectiveness. For the experiment shown in FIG. 3, a panel of microparticles were synthesized that were coated with different ratios of EFNB1 and EFNB2, ranging from 100% EFNB1 (0% EFNB2), to 0% EFNB1 (100% EFNB2). In FIG. 3a, the microparticles were incubated with pseudotyped virus at 37° C., and FACS analysis performed to quantify the inhibition of viral infectivity. The top section of the panels represents the infected cells. In the experiments shown in FIGS. 3b and 3c, the microparticles were incubated with purified soluble HeV G at 37° C. (b) or at 4° C. (c), and the presence of HeV G on the microparticles was quantified by FACS analysis. The microparticles bearing higher concentrations of EFNB2 efficiently bound HeV G and were fluorescent, while the microparticles bearing the most EFNB1 did not bind HeV G. The binding of soluble HeV G to the microparticles increased as the ratio of EFNB2:B1 increased, and was equivalent at 37° C. and at 4° C. Strong viral inactivation occurred with 50% EFNB2 at 37° C., even though binding of soluble HeV G to the microparticles at the equivalent condition was reduced. Likewise, little viral inactivation occurred at 4° C. (FIG. 2a) though binding of soluble HeV G is equivalent at 37° C. and at 4° C. (FIGS. 3b and 3c). The results suggest that, in addition to the binding of receptor (e.g., EFNB2) and the viral receptor-binding protein (e.g., HeV G), viral inactivation by the EFNB2-coated microparticles requires an additional step, which may be the inopportune activation of F protein.

The receptor-coated microparticles inactivated pseudotyped viruses specifically, effectively and renewably. Microparticles that bear the entry receptor for henipaviruses, EFNB2, reduce the titer of infective virus in cell culture. The inhibition is specific: only EFNB2-bearing, but not EFNB1-bearing, microparticles are inhibitory, and the inhibitory effect is specific for henipaviruses. The inhibitory activity of the microparticles is temperature dependent: viral infection of cultured cells is specifically inhibited after being incubated with microparticles at 37° C. but not at 4° C. The microparticles are not saturable, and, therefore, can be re-used to inactivate or inhibit viruses.

Experimental Methods

Cells and Viruses.

293T (human kidney epithelial) and Vero (African green monkey kidney cells) were grown in Dulbecco's modified Eagle's medium (DMEM) (Mediatech; Cellgro) supplemented with 10% fetal bovine serum and antibiotics in 5% $CO_2$.

Plasmids and Reagents.

To generate the shortened cytoplasmic tail variant of HeV G (HeV G-CT32), an internal primer containing an EcoR1 site and initiating at position 32 of the open reading frame was used for nested PCR. Porotto, et al Inhibition of Hendra virus membrane fusion. *J. Virol.* 80, 9837-9849 (2006). The primer sequence was: 5' GGAATTCGGCACAATGGACATCAAG 3' (SEQ ID NO:1). To generate a soluble form of HeV G, the extracytoplasmic domain of G was subcloned into pSEC-tag (Invitrogen). Negrete, et al. EphrinB2 is the entry receptor for Nipah virus, an emergent deadly paramyxovirus. *Nature* 436, 401-405 (2005).

Transient Expression of G and F.

Transfections were performed according to the Lipofectamine 2000 reagent manufacturer's protocols (Invitrogen).

Rabbit Polyclonal Antibodies.

Anti-HeV G and anti-HeV F polyclonal antibodies were raised in rabbit by DNA immunization of HeV G or HeV F (Genovac).

Pseudotyped Virus Infection Assay.

The VSV-ΔG-RFP is a recombinant VSV derived from the cDNA of VSV Indiana, in which the G gene is replaced with the red fluorescent protein (RFP) gene. Pseudotypes with HeV F and G were generated as described. Negrete, et al. EphrinB2 is the entry receptor for Nipah virus, an emergent deadly paramyxovirus. *Nature* 436, 401-405 (2005). Takada, et al. A system for functional analysis of Ebola virus glycoprotein. *Proceedings of the National Academy of Sciences of the United States of America*, 94, 14764-14769 (1997). Briefly, 293T cells were transfected with plasmids encoding either VSV-G, HeV G-CT32 only, HeV F only, or HeV G-CT32 plus HeV F. 24 hrs post-transfection, the dishes were washed and infected with VSV-ΔG-RFP complemented with VSV G (m.o.i. of 1). Supernatant containing pseudotyped viruses (HeV F/CT32-G or VSV-G) was collected 24 hrs post-infection and stored at −80° C.

Pseudotyped viruses were incubated with microparticles or control agarose beads before being used to infect Vero or 293T cells. RFP production at 24 hrs or 36 hrs was analyzed by fluorescent microscopy and FACS (Becton Dickinson FACSCalibur). Porotto, M., et al. Inhibition of parainfluenza type 3 and Newcastle disease virus hemagglutinin-neuraminidase receptor binding: Effect of receptor avidity and steric hindrance at the inhibitor binding sites. *Journal of Virology* 78, 13911-13919 (2004). The number of fluorescent cells (from the RFP signal) after being incubated with pseudotyped viruses not treated with the microparticles represented maximal infection (i.e., 0% viral infectivity inhibition). The number of fluorescent cells not incubated with pseudotyped viruses represented 100% viral infectivity inhibition. The percentage of viral infectivity inhibition was then calculated accordingly.

Microparticle Reagents.

Mesoporous silica microparticles with diameters of about 10 μm or 3 μm were purchased from GFS, each with pores about 10 nm in mean diameter. 1-palmitoyl-2-oleyl-sn-glycero-3-phosphocholine (POPC) and a nickel-chelating lipid, the nickel salt of 1,2-dioleoyl-sn-glycero-3-{[N(5-amino-1-carboxypentyl)iminodiacetic acid] (DOGS-NTA-Ni), were purchased from Avanti Polar Lipids (Alabaster, Ala.) and dissolved in chloroform to form solutions of 10 mg/ml and 1 mg/ml, respectively. Red fluorescent dye, 1,2-dihexadecanoyl-sn-glycero-3-phosphoethanolamine, triethylammonium salt (Texas-red DHPE), was purchased from Invitrogen. Histidine-tagged EFNB2 and EFNB1 were purchased from Sigma-Aldrich and hydrated following the manufacturers protocol. Alexa Fluor 488 donkey anti-rabbit IgG was purchased from Sigma-Aldrich. Phosphate buffered saline (PBS) for washing and formation of lipid vesicles was made by diluting 100 ml cell-culture grade 1×PBS with 400 ml of deionized (DI) water.

Mesoporous Silica Cores.

Silica nanoparticles were prepared by the Stober method. Commercially purchased mesoporous silica microparticles were treated to form a hydrophilic surface before use. The microparticles were stirred for 10 min at 85° C. in 4% hydrogen peroxide and 4% ammonium hydroxide, in water, followed by repeated centrifugation and washing with DI water, stirring for 10 min at 85° C. in 4% hydrogen peroxide and 0.4 mol/L hydrochloric acid (HCl), in water, followed again by repeated centrifugation and washing with DI water. The final microparticle concentration was adjusted to $\approx 10^8$ microparticles/mL.

Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

SEQUENCE LISTING

```
<160> NUMBER OF SEQ ID NOS: 1

<210> SEQ ID NO 1
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 1
ggaattcggc acaatggaca tcaag                                          25
```

Unilamellar Lipid Vesicles.

POPC was mixed with 5% DOGS-NTA-Ni in a glass vial. 1% fluorescent Texas-red DHPE was included for selected experiments to confirm coating of the microparticles with lipids. The solvent was removed using a nitrogen stream, before the vial was kept under vacuum for 1 h to 2 h to remove residual solvent. The lipid film was hydrated using DI water overnight at 4° C. The final lipid concentration was adjusted to 2 mg/ml. The hydrated lipids were vortexed for several minutes and were extruded using a mini-extruder (Avanti Polar Lipids) with 0.1 μm polycarbonate membrane filters (Whatman, Inc., Newton, Mass.). The lipid solution was passed through the extruder at least 19 times and diluted with PBS to 1 mg/ml.

Lipid Coating of the Microparticles.

1 ml silica microparticle suspension was centrifuged and the supernatant removed. 1 ml of the freshly prepared small unilamellar vesicle solution was added to the microparticles and incubated with shaking for 45 min to obtain silica microparticle supported lipid bilayers. The final mixture was repeatedly centrifuged and washed in PBS to remove excess lipid.

Addition of Receptor Moieties.

Lipid-coated microparticles were incubated with 50 μl of 100 μg/ml of EFNB2 (or EFNB1 for control samples) in PBS at room temperature for 20 min followed by repeated centrifugation and washing in PBS to remove excess protein. Each of the 3 μm diameter microparticles has approximately $10^4$ copies of EFNB2.

The scope of the present invention is not limited by what has been specifically shown and described hereinabove.

What is claimed is:

1. A method of inactivating a *Henipavirus* comprising the steps of:
    contacting the virus with a carrier matrix at 37° C., wherein lipids are attached to the carrier matrix, wherein at least one virus-specific cellular receptor is attached to the lipids, and wherein the cellular receptor is EphrinB2 (EFNB2);
    binding the virus-specific cellular receptor to at least one viral receptor-binding protein at 37° C. to activate a viral fusion protein of the virus, thereby inactivating the virus without completing a fusion between the virus and the carrier matrix, wherein the viral receptor-binding protein is *Henipavirus* G protein, and wherein the viral fusion protein is *Henipavirus* F protein; and
    releasing the inactivated virus from the carrier matrix, wherein viral infectivity is reduced at least 50%.

2. The method of claim 1, wherein the lipids are selected from the group consisting of phospholipids, fatty acids, sterol lipids, glycerolipids, sphingolipids, prenol lipids, saccharolipids, polyketides and combinations thereof.

3. The method of claim 1, wherein the lipids comprise phosphatidylcholine.

4. The method of claim 1, wherein the lipids form a lipid bilayer.

5. The method of claim 1, wherein the carrier matrix is a particle.

6. The method of claim 5, wherein the particle is a silica particle.

7. The method of claim 5, wherein the particle is a nickel, polystyrene or latex particle.

8. The method of claim 5, wherein the particle has a diameter between about 1 nm and about 100 μm.

9. The method of claim 8, wherein the particle has a diameter between about 10 nm and about 50 μm.

10. The method of claim 1, wherein the carrier matrix comprises pores from about 1 nm to about 100 nm in mean diameter.

11. The method of claim 1, wherein at least one therapeutic agent is further attached to the carrier matrix.

12. The method of claim 11, wherein the therapeutic agent is an antiviral agent selected from the group consisting of a neuraminidase inhibitor, a viral fusion inhibitor, a protease inhibitor, a DNA polymerase inhibitor, a signal transduction inhibitor, a reverse transcriptase inhibitor, an interferon, and a virus-specific siRNA.

13. The method of claim 1, wherein the carrier matrix is non-saturable.

14. The method of claim 1, wherein the carrier matrix is re-usable.

* * * * *

UNITED STATES PATENT AND TRADEMARK OFFICE
CERTIFICATE OF CORRECTION

PATENT NO.        : 9,732,324 B2
APPLICATION NO.   : 13/125756
DATED             : August 15, 2017
INVENTOR(S)       : Anne Moscona et al.

Page 1 of 1

It is certified that error appears in the above-identified patent and that said Letters Patent is hereby corrected as shown below:

In the Specification

Column 1, Line 9, after "CROSS REFERENCE TO RELATED APPLICATION", please insert:

--STATEMENT REGARDING FEDERALLY SPONSORED RESEARCH OR DEVELOPMENT
This invention was made with government support under Grant Number EY016570 awarded by the National Institutes of Health. The Government has certain rights in the invention.--

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*